(12) United States Patent  
Farquharson

(10) Patent No.: US 7,312,088 B2
(45) Date of Patent: Dec. 25, 2007

(54) METHOD AND APPARATUS FOR PERFORMING SERS ANALYSIS USING A CHEMICAL REFERENCE

(75) Inventor: Stuart Farquharson, Meriden, CT (US)

(73) Assignee: Real-Time Analyzers, Inc., East Hartford, CT (US)

( * ) Notice: Subject to any disclaimer, the term of this patent is extended or adjusted under 35 U.S.C. 154(b) by 400 days.

(21) Appl. No.: 10/902,511

(22) Filed: Jul. 29, 2004

(65) Prior Publication Data

US 2005/0266584 A1 Dec. 1, 2005

Related U.S. Application Data

(63) Continuation-in-part of application No. 10/854,134, filed on May 26, 2004, now abandoned.

(51) Int. Cl.
*G01N 21/77* (2006.01)
(52) U.S. Cl. ............... 436/169; 436/164; 436/166; 436/169; 422/56; 422/57; 422/58; 422/82.05
(58) Field of Classification Search ............... None
See application file for complete search history.

(56) References Cited

OTHER PUBLICATIONS

Cabalin et al. "Flow-injection analysis and liquid chromatography: surface-enhanced Raman spectrometry detection by using windowless flow cell", Analytica Chimica Acta, 1996.*
Cabalin et al. "Surface-enhanced Raman spectrometry for detection in liquid chromatography using a windowless flow cell", Talanta, 1993, v. 40,, No. 11, pp. 1741-1747, Abstract.*
Nirode et al. "On-column surface-enhanced Raman spectroscopy detection in capillary electrophoresis using running buffers containing silver colloidal solutions", Anal. Chem., 2000, v. 72, pp. 1866-1871.*
Farquharson et al. "Simultaneous chemical separation and surface-enhanced Raman spectral detection using silver-doped sol-gels", Applied Spectroscpy, 2003, . 57, No. 4, pp. 479-481.*
Farquharson et al. "Rapid dipicolinic acid extraction from *Bacillus spores* detected by surface-enhanced Raman spectroscopy", Applied Spectroscopy, 2004, v. 53, No. 3, pp. 351-354.*

* cited by examiner

*Primary Examiner*—Yelena G. Gakh
(74) *Attorney, Agent, or Firm*—Tra S. Dorman

(57) ABSTRACT

Apparatus for use in effecting surface-enhanced Raman spectroscopy comprises first and second containment means, the first containment means containing a known quantity of a reference chemical having an effective surface-enhanced Raman factor, and the second containment means containing a surface-enhanced Raman-active medium and being sufficiently transparent, at least at one optical access location, to permit both the excitation irradiation of, and also the collection of surface-enhanced Raman scattered radiation from, a common field of view of the surface-enhanced Raman-active medium. The apparatus is constructed for carrying out the method of the invention; i.e., for effecting intimate mixing, substantially prior to introduction to the surface-enhanced Raman-active medium contained in the second containment means, of the reference chemical with an analyte chemical-containing solution introduced through an entrance into the first containment means. The homogeneous test solution so formed permeates the SER-active material in the second containment means, which is irradiated at the common field of view so as to produce SER scattered radiation for collection and quantitative analysis.

26 Claims, 2 Drawing Sheets

METHOD AND APPARATUS FOR PERFORMING SERS ANALYSIS USING A CHEMICAL REFERENCE

CROSS REFERENCE TO RELATED APPLICATION

This application is a continuation-in-part of U.S. application Ser. No. 10/854,134, filed May 26, 2004 now abandoned and entitled "Method for Quantitative Surface-Enhanced Raman Spectroscopy Using a Chemical Reference."

STATEMENT REGARDING FEDERALLY SPONSORED RESEARCH AND DEVELOPMENT

The United States Government has rights in this invention pursuant to USDA Contract No. 2002-33610-11815, NIH Contract No. 1R43CA94457-01 and NSF Contract No. DMI-0215819.

BACKGROUND OF THE INVENTION

Surface-enhanced Raman spectroscopy (SERS) has proven to be one of the most sensitive methods available for trace chemical analysis by detecting single molecules (see Kneipp, K., Wang, Y., Dasari, R. R., and Feld, M. S., "Approach to Single-Molecule Detection Using Surface-Enhanced Resonance Raman Scattering (SERRS): A Study Using Rhodamine 6G on Colloidal Silver", *Applied Spectroscopy*, 49, 780-784 (1995) or Nie, S. and S. R. Emory, "Probing Single Molecules and Single Nanoparticles by Surface Enhanced Raman Scattering", *Science*, 275, 1102 (1997)). In addition to sensitivity, the rich molecular vibrational information provided by Raman scattering yields exceptional specificity and allows identifying virtually any chemical as well as distinguishing multiple chemicals in mixtures (see Garrel, R. L., "Surface-Enhanced Raman Spectroscopy," *Analytical Chemistry*, 61, 401A-411A (1989) or Storey, J. M. E., Barber, T. E., Shelton, R. D., Wachter, E. A., Carron, K. T., and Jiang, Y. "Applications of Surface-Enhanced Raman Scattering (SERS) to Chemical Detection", *Spectroscopy*, 10(3), 20-25 (1995)). SERS involves the absorption of incident laser photons, generating surface plasmons within nanoscale metal structures, which then couple with nearby molecules (the analyte chemical), to thereby enhance the efficiency of Raman scattering by six orders of magnitude or more (Jeanmaire, D. L., and R. P. Van Duyne, "Surface Raman Spectroelectrochemistry", *J. Electroanal. Chem.*, 84, 1-20 (1977) or Weaver, M. J., Farquharson, S., Tadayyoni, M. A., "Surface-enhancement factors for Raman scattering at silver electrodes. Role of adsorbate-surface interactions and electrode structure", *J. Chemical Physics*, 82, 4867-4874 (1985)).

Previous research has employed primarily the three most common methods of generating SERS, using: (1) activated electrodes in electrolytic cells (see for example Jeanmaire or Weaver, supra); (2) activated silver and gold colloid reagents (Kerker, M., O. Siiman, L. A. Bumm, D.-S. Wang, "Surface-enhanced Raman Scattering of citrate ion adsorbed on colloidal silver", *Applied Optics*, 19, 3253-3255 (1980) or Angel, S. M., L. F. Katz, D. D. Archibold, L. T. Lin, D. E. Honigs, "Near Infrared Surface-enhanced Raman Spectroscopy. Part II: Copper and gold colloids", *Applied Spectroscopy*, 43, 367 (1989)); or (3) activated silver and gold substrates (Seki., H., "Surface-enhanced Raman Scattering of pyridine on different silver surfaces", *J. Chemical Physics*, 76, 4412-4418 (1982) or Li, Y.-S., T. Vo-Dinh, D. L. Stokes, Y. Wang, "Surface-Enhanced Raman Analysis of p-Nitroaniline on Vacuum Evaporation and Chemical Deposited Silver-Coated Alumina Substrates", *Applied Spectroscopy*, 46, 1354 (1992)).

However, none of the foregoing techniques is capable of providing sufficiently reproducible measurements to enable the use of SERS for quantitative analysis. This is largely due to the inability to reproducibly manufacture a surface-enhanced Raman-active medium. More specifically, the first technique referred to above uses electrodes that are "roughened" by changing the applied potential between oxidation and reduction states; it is found that the desired metal surface features cannot be reproduced faithfully from one roughening procedure to the next. In the second technique referred to, colloids are prepared by reducing a metal salt solution to produce metal particles, which in turn form aggregates. Particle size and aggregate size are strongly influenced by initial chemical concentrations, temperature, pH, and rate of mixing, and again therefore the desired features are not reproducible. Finally, the third technique mentioned uses substrates that are prepared by depositing the desired metal onto a surface having the appropriate roughness characteristics. To permit the analysis, the sample is preferably dried on the surface to concentrate the analyte on the active metal, and once again replication is difficult to achieve. The relative merits of the three methods for preparing SER-active surfaces, described above, have been further reviewed by K. L. Norrod, L. M. Sudnik, D. Rousell, and K. L. Rowlen in "Quantitative comparison of five SERS substrates: Sensitivity and detection limit," *Applied Spectroscopy*, 51, 994-1001 (1997).

As disclosed by Farquharson et al. in U.S. Pat. No. 6,623,977 (issued Sep. 23, 2003 and of common assignment herewith, and published as International Publication No. WO 01/33189 A2, dated 10 May 2001), the entire specification of which is hereby incorporated by reference thereto, sol-gels have been developed to trap particles of silver or gold (or of certain other metals) to provide an improved medium for reproducibly generating surface-enhanced Raman (SER) scattering. It is appreciated that the particle size and aggregation state of the metal dopant are stabilized, once the sol-gel has formed, and that the sample and/or solvent will not alter the plasmon-generating capabilities of the trapped metal particles. Albeit changes in pH may still result in variable Raman signal intensities, such as in the case of weak acids and bases where the relative concentrations of the ionized and non-ionized forms may be influenced, Farquharson et al. have demonstrated reasonably reproducible measurements, whereby some 36 repeat measurements of the same chemical, using multiple glass vials coated with silver-doped sol-gels, yielded a standard deviation of ~15% (Farquharson, S., Gift, A., Maksymiuk, P., Inscore, F., Smith, W., Morrisey, K., and Christesen, S. D., "Chemical agent detection by surface-enhanced Raman spectroscopy", *SPIE*, 5269, 16-22 (2003). Transmission electron micrographs have shown however that the distribution of metal particles within the sol-gel is inhomogeneous, which will cause variation in the SER-activity, as a function of the position of the excitation laser focal spot on the sol-gel, and is a likely source of the observed variations of SER spectral band intensities.

Quantitative measurements are of course fundamental to analytical chemistry, and most instruments and methods currently employed require some form of calibration to ensure the accuracy of measurements made. In the case of Raman spectroscopy, the intensities of spectral bands, or peaks, present in the scans produced are directly proportional to the concentrations of the analytes being measured. A measurement of the intensity of such bands, as either peak height or peak area, for a chemical of known concentration can therefore be used to calculate the concentration of the same chemical in an unknown sample, by measuring its corresponding spectral band intensities. Variations in laser power, detector response, ambient temperature, etc. can however influence the intensity of the spectral bands and thereby introduce significant error in the quantitative calculation.

A useful method of overcoming such variation errors involves the inclusion of a chemical of known concentration in the unknown sample, and using its Raman spectral band intensity as a reference to the band intensity of the chemical of unknown concentration (Pelletier, M. J., Ed. "Analytical Applications of Raman Spectroscopy," Blackwell Science Ltd., London, 1999, p. 20). The choice of internal reference chemical employed depends somewhat upon the nature of the sample that is to be measured, but it is important that the spectral bands of the reference chemical that are to be used for quantifying the concentration should not overlap the spectral bands of the unknown sample to a degree that would interfere with the quantitative calculation. The prior art does not address the variability of amount of Raman scattering enhancement produced by surface-enhanced Raman-active media and, in any event, does not disclose reference chemicals, or provide suitable referencing techniques, that are specific to SERS or to measurement and analytical methods based thereupon.

SUMMARY OF THE INVENTION

Accordingly, the broad objects of the present invention are to provide a novel apparatus for effecting SERS, whereby precisely reproducible SER spectral measurements can readily be derived, and to provide a novel method utilizing the same.

Other objects of the invention are to provide such an apparatus and method wherein and whereby the need for exact replication and stable maintenance of the SER-active materials is obviated, so as to enable consistent and substantially invariant SER-scattering analyses to be made.

Additional objects of the invention are to provide such an apparatus and method by which is enabled the detection and quantification of analytes in very low quantities or concentrations, in a manner that is highly effective, precise, reliable, facile and convenient.

It has now been found that certain of the foregoing and related objects of the invention are attained by the provision of apparatus for use in effecting surface-enhanced Raman spectroscopy, comprising first and second containment means, the first containment means having a liquid-flow entrance thereinto and an exit therefrom and containing a known quantity of a reference chemical having an effective surface-enhanced Raman factor. The second containment means contains a surface-enhanced Raman-active medium having a liquid-flow entrance thereinto, operatively connected to the exit from the first containment means, and an exit therefrom, the second containment means being sufficiently transparent, at least at one optical access location, to permit both the excitation irradiation of, and also the collection of surface-enhanced Raman scattered radiation from, a common field of view of the surface-enhanced Raman-active medium contained therewithin. The apparatus is constructed for effecting intimate mixing, substantially prior to introduction to the surface-enhanced Raman-active medium contained in the second containment means, of the reference chemical with an analyte chemical-containing solution introduced through the entrance into the first containment means.

In certain embodiments, the apparatus will additionally include a separate mixing chamber operatively interposed between the first and second containment means, or the first containment means may itself comprise a mixing chamber. The first and second containment means will typically be tubular sections, such as capillaries. The apparatus may additionally include a third containment means having an entrance thereto operatively connected to the exit from the second containment means, with the third containment means serving as an overflow chamber.

In many instances, the reference chemical will preferably be in the form of a solid mass that is completely and readily soluble in the analyte chemical-containing solution to form a homogeneous test solution. Alternatively, the reference chemical may be in the form of a solution with which the analyte chemical-containing solution is completely soluble to form a homogeneous test solution. The apparatus will normally additionally include liquid transport means operatively connected to the entrance into the first containment means, for injecting or drawing the analyte chemical-containment solution thereinto, and/or to the exit from the second containment means for effecting evacuation thereof, such liquid transport means advantageously comprising a syringe.

Other objects of the invention are attained by the provision of a method for effecting surface-enhanced Raman spectroscopy utilizing apparatus of the kind herein described. In carrying out the method positive and/or negative pressure is applied so as to cause a known volume of a solution containing at least one analyte chemical, in an unknown concentration, to be introduced into the first containment means of the apparatus; so as to cause a reference chemical contained in the first containment means to disperse homogeneously with the analyte-containing solution; and so as to cause the homogeneous test solution to be transported into the second containment means and to permeate the surface-enhanced Raman-active medium contained therein. The surface-enhanced Raman-active medium, permeated by the homogeneous test solution, is then irradiated with excitation radiation so as to produce surface-enhanced Raman scattered radiation at a common field of view of the surface enhanced Raman-active medium, and a measurable amount of the surface-enhanced Raman scattered radiation emanating from the common field of view is collected for analysis.

In certain preferred embodiments of the method the reference chemical contained in the first containment means will be in the form of a solid mass that is completely and readily soluble in the analyte chemical-containing solution, and the step of dispersing will be effected with the analyte chemical-containing solution flowing in intimate contact with the reference chemical mass. In other embodiments the reference chemical will be in the form of a solution with which the analyte solution is completely soluble, and the step of dispersing will be effected by mixing the two solutions, usually by introducing the analyte chemical-containing solution into the reference chemical solution.

As used herein the phrase "surface-enhanced Raman factor" (or "SER factor") represents the quotient of the surface-enhanced Raman response of the molecule in question divided by its normal (i.e., non-surface enhanced) Raman response in the same solution. To be effective in the practice of the present invention, the reference chemical must have an SER factor of at least 100. As a practical matter, however, the SER factor of the reference chemical will usually be at least 1,000, and it will often (and most desirably) be on the order of one million or larger; stated alternatively, the surface-enhanced Raman response of the reference chemical will be at least two-, preferably at least three-, and most desirably upwardly of six-orders of magnitude greater than its normal Raman response.

The phrase "common field of view" should be understood to mean the single field of surface-enhanced Raman-active medium at which both the reference chemical and also the analyte chemical are simultaneously irradiated by the excitation (generally, laser beam) radiation, and the field from which SER scattered radiation is also collected, and it will be understood that collection will usually occur on the same axis as the axis of irradiation. The term "scattering efficiency" refers to the ratio of Raman radiation energy produced per unit of excitation radiation energy delivered.

The normal Raman scattering effect of the reference chemical employed must not only be susceptible to substantial surface enhancement, but the reference chemical should also have a Raman spectral response that is non-interfering with the Raman spectral response of the analyte chemical (or chemicals) that is (or that are) the subject of the analysis; i.e., the reference chemical should produce surface-enhanced Raman spectral bands that do not substantially overlap the characterizing, surface-enhanced Raman spectral band of the "at least one" analyte chemical involved. Moreover, the molecular size of the reference chemical should be substantially smaller (typically being at least two orders of magnitude smaller) than is that of the analyte chemical, and preferably the reference chemical will be of such size that it occupies no more than about one percent of the surface area of a metal constituting the surface-enhanced Raman active medium. In most instances the reference chemical will comprise a thiocyanate or cyanide compound that is soluble in the test solution, usually being a salt or an inorganic complex and desirably being selected from the group consisting of thiocyanate salts of sodium, potassium and calcium; cyanide salts of sodium, potassium and calcium; sodium ferrocyanide; potassium hexacyanoruthenate; and pentacyanoferrothiocyanate.

The surface-enhanced Raman-active medium used will normally employ a metal selected from the group consisting of copper, gold, silver, nickel, and alloys and mixtures thereof to produce particles (normally 5 to 1000 nm diameter particles), isolated or aggregated, ordered or random, or to produce a surface of equivalent morphology (e.g., roughened electrodes, periodic arrays, patterned structures). The particles can be generated on a surface by chemical- or vapor-deposition techniques; functionally equivalent surface morphologies can be generated by chemical or electrochemical etching, and effective surface structures can be generated by photolithography or a combination of the foregoing techniques (e.g., vapor deposition on chemically deposited spheres). Metal particles or aggregates can be suspended in a colloidal solution, by reduction of a metal salt solution, for use as such or for application, for example, to a surface bearing the analyte chemical.

The metal particles or aggregates can also be incorporated into porous structures, such as polymers or sol-gels. Polymers can be synthesized with at least one monomer that allows inclusion of the metal constituent, and at least one chemical functional group that maintains porosity, or provides for porosity (e.g., a polymer that expands, upon the addition of a solvent, to allow access to the metal surface by the analyte).

In certain preferred embodiments, the surface-enhanced Raman-active medium will comprise a chemically synthesized sol-gel, desirably synthesized utilizing a silicia-based, titania-based, or zirconia-based alkoxide and at least one surface-enhanced Raman-active metal.

In other preferred embodiments, in which the surface-enhanced Raman-active medium is comprised of a mixture of a porous material and at least one surface-enhanced Raman-active metal, the porous material employed is desirably one that is effective to produce chemical separations or selective chemical extractions. Such a porous material may be selected from the group consisting of sol-gels, silica gels, silica stabilized by zirconia, derivatized silica-based matrices (e.g., trifunctional quanternary amine, aromatic sulfonic acid), long-chain (e.g., $C_8$, $C_{18}$) alkane particles, derivatized long-chain alkane particles (e.g., phenyl, cyano, etc.).

In the practice of the present invention, the measured intensity of the characteristic band of the analyte chemical, divided by the measured intensity of the characteristic band of the reference chemical, provides a ratio factor that is employed to eliminate the effects of parameters that cause variations in surface-enhanced Raman activity of the selected surface-enhanced Raman-active medium, and is utilized to calculate the concentration of the analyte chemical. The surface-enhanced Raman scattering efficiencies of the reference chemical and of the analyte chemical, relative to one another, is also utilized to calculate the analyte chemical concentration.

The relative scattering efficiencies can be determined by measuring surface-enhanced Raman spectral band intensities of the reference and analyte chemicals, using a standard sample containing a representative surface-enhanced Raman-active medium and a standard solution containing selected concentrations of the two chemicals. Calculation of the unknown concentration can be carried out by application of the following equation (Equation I):

$$[AMeas] = (I^{SER}_{AMeas}/I^{SER}_{RMeas}) \times (I^{SER}_{RS}/I^{SER}_{AS}) \times [RMeas],$$

wherein AMeas stands for the analyte chemical in the test solution and [AMeas] represents the concentration thereof, $I^{SER}$ stands for the measured intensity of the surface-enhanced Raaman band used for the scattering efficiency determination, RMeas stands for the reference chemical in the test solution and [RMeas] represents the concentration thereof, RS stands for the reference chemical of selected concentration, in the standard solution, and AS stands for the analyte chemical of selected concentration therein; the term $(I^{SER}_{RS}/I^{SER}_{AS})$ provides the relative surface-enhanced Raman scattering efficiency ratio of the reference chemical and the analyte chemical.

An underlying concept of the method of the invention concerns the use of a chemical of known concentration (the reference chemical), as a surface-enhanced Raman activity standard to which the unknown concentration of an analyte chemical can be referenced, and thereby quantitatively determined, by correlation of respective spectral band intensities. In some instances the surface enhancement provided by the reference chemical will advantageously be of known or measurable magnitude; generally, however, only the concentration of the reference chemical and the signal intensity associated with it need be known.

The reference chemical must not only exhibit an effective SER factor, but it should also be of such molecular size that it occupies only a small percentage of the SER-active metal surface within the SER experimental field of view, and thereby produces a SER signal, when irradiated or illuminated, having an intensity that is indicative of the amount of SER activity within that field of view. The analyte chemical, which necessarily also occupies a portion of the metal surface within the same, common field of view, will of course experience the same amount of SER activity. The intensity of a suitable SER spectral band of the analyte chemical, of unknown concentration, divided by the intensity of a suitable SER spectral band of the reference chemical, of known concentration, will thus provide a factor by which the effects of parameters that cause variations in SER-activity (such as differences in the average particle size, the particle size distribution, and the extent and variety of particle aggregation) can be minimized or negated entirely. Furthermore, this ratio factor will provide a method for calculating, quantitatively, the concentration of the analyte chemical of unknown concentration, provided the SER scattering efficiencies of the two chemicals, relative to one another, are known; the relative scattering efficiency factor is easily obtained by performing an SERS measurement of a sample in which the concentrations of both chemicals are known.

The concentration of the analyte of unknown concentration can be calculated by application of Equation I, hereinabove set forth and defined. It is noted that the use of Equation I enables quantitative measurements to be performed with an exceptional level of precision.

In accordance with one specific and preferred embodiment of the invention, trace quantities (typically 1-10 ppm) of sodium or potassium thiocyanate are added to samples of unknown analyte concentration as the internal intensity reference chemical, utilizing the techniques herein described. Both salts dissociate completely in water, as well as in other polar solvents, to produce the linear $SCN^-$ molecule, which has only four unique molecular vibrations, two degenerate bending modes and the SC and CN stretching modes, occurring in the Raman spectrum as bands or peaks at 465 (degenerate), 750, and 2080 $cm^{-1}$, respectively. The degenerate bending modes have very little band intensity. Similarly, SER spectra of the $SCN^-$ molecule include bands representing these same modes, albeit shifted in frequency and changed in intensity due to the interaction with the surface. In the case of silver as the SER-active metal, the degenerate modes are observed at 445 $cm^{-1}$ with modest intensity, and the SC stretch shifts to 735 $cm^{-1}$ and loses intensity, while the CN stretch shifts to 2095 $cm^{-1}$ and remains the most intense peak. A band at 900 $cm^{-1}$ may also be observed, due to the generation of boric acid during the reduction of silver in certain techniques used to produce the surface-enhanced Raman material. Since the CN stretching mode dominates the spectrum it is ideal for use as the intensity reference.

A full Raman or SER spectrum covers the spectral range of 0 to 4000 $cm^{-1}$, and thus almost the entire spectrum is available to observe bands generated by other chemicals (analytes) that might be the subject of a quantitative measurement. In particular, the region from 600 to 1600 $cm^{-1}$, most often used to identify unknown chemicals and known as the "fingerprint region," is almost completely available for analysis, with only minor interference from the relatively weak SCN band at 740 $cm^{-1}$. Furthermore, only two molecular vibrations commonly occur between 1900 and 2600 $cm^{-1}$, i.e., the C≡N, and the C≡C vibrations, and therefore only molecules containing these functional groups can potentially interfere with the use of the $SCN^-$ molecule as an intensity reference.

As noted above, the SER band for $SCN^-$ at 2095 $cm^{-1}$ is exceptionally strong, and is easily observed using as little as 10 ppm (10 microgram of $SCN^-$ per milliliter of water). At this extremely low concentration the possibility of a reaction occurring between the reference chemical and the analyte is correspondingly unlikely. Furthermore, the $SCN^-$ anion is very small, and each molecule can be shown to typically occupy only about 0.01 $nm^2$ of the SER-active metal surface, leaving the vast majority of the metal surface available for occupancy by the molecules to be analyzed, as is of course important to ensure that enhancement of the anlayte Raman scattering can occur.

A SER spectral measurement of a homogeneous mixture of two chemicals, one an analyte of unknown concentration and one of $SCN^-$ of 10 ppm, will produce a spectrum of Raman bands according to the molecular structure of the analyte and the $SCN^-$ anion. More importantly, the ratio of the intensities of the analyte spectral bands and the SCN bands, preferably the CN stretch at 2095 $cm^{-1}$ for the latter, will be constant and independent of the location in the sample at which the laser is effective to generate SER scattering. As noted above, a measurement of a mixture of the analyte in question, and $SCN^-$, both in known concentrations (e.g., of 10 ppm), will establish the relative SER scattering efficiencies of the two chemicals and thereby enable the unknown concentration of the same analyte, in any sample containing the reference chemical in a known concentration, to be determined.

In another specific embodiment of the methodology, a trace quantity of sodium or potassium cyanide is introduced, as the internal intensity reference, into a sample containing an unknown concentration of analyte chemical. Both salts completely dissociate in water, as well as in other polar solvents, forming the linear $CN^-$ anion, which has one unique molecular vibration observed in the normal Raman spectra at 2080 $cm^{-1}$. In the SER spectra this mode is shifted similarly to $SCN^-$, by interaction with the SER-active metal, to 2095 $cm^{-1}$ in the case of silver; the same interaction produces a spectral band at 260 $cm^{-1}$ as well. The 260 $cm^{-1}$ band is relatively weak, while the 2095 $cm^{-1}$ band produces an exceptionally strong SER response on either gold or silver and thus is ideal for use as the intensity reference. Because of its relatively high toxicity, however (i.e., as reported in *The Merck Index*, a dose of $SCN^-$ that is lethal to 50% of test rats ($LD_{50}$) is 854 mg/kg, whereas the $LD_{50}$ for $CN^-$ is 2.5 mg/kg), the use of cyanide salts may often be limited to those applications in which the thiocyanate salts are, for some reason, problematic.

Other compounds that produce suitable SER reference bands may of course also be employed as reference chemicals, provided the criteria set forth herein are satisfied. For example, calcium-, cuprous-, nickel-, platinum-, and zinc-cyanide or thiocyanate, and potassium or sodium ferri- or ferro-hexacyano complexes, may produce such reference bands as will render them useful in the present method. Furthermore, for those molecules containing an acetylene functionality (e.g. phenyl acetylene) that could produce an SER spectral interfering band, the C≡C stretch has been observed between 1990 and 2025 $cm^{-1}$, which would not overlap the CN stretching band.

To enable automatic chemical introduction and mixing in accordance with the present invention, a microchip can incorporate a closed compartment containing a predefined amount of a solution of the reference chemical, at a known concentration, to which compartment a predefined amount of analyte solution is added, for example by puncturing or rupturing a frangible seal and injection of the analyte solution from a syringe, to effect mixing. Alternatively, a weighed amount of reference chemical, in the solid phase, can be placed or contained in a first compartment or segment of a flow system (e.g., a capillary), which compartment is joined to a second compartment comprising a mixing chamber and, in turn, to a third compartment containing a SER-active medium. Such a flow system may, more specifically, comprise a 1-mm diameter glass capillary, containing a measured amount of KSCN, joined to a 1 mL volume bulb and, in turn, to a 1-mm diameter glass capillary containing a metal-doped sol-gel, connected to a syringe. In use, 1 mL of the analyte of unknown concentration would be drawn through the KSCN mass, dissolving it and intermixing with it in the adjacent bulb, the mixture then being drawn into the SER-active sol-gel by the syringe; a fixed sample volume, or a fixed plunger travel-limiting element on the syringe, would define the precise volume of the analyte solution that is sampled, mixed, and analyzed.

DETAILED DESCRIPTION OF THE PREFERRED AND ILLUSTRATED EMBODIMENTS

As discussed above, the method of the invention employs a reference chemical of known concentration as a surface-enhanced Raman activity standard, to which the concentrations of unknown samples can be referenced, utilizing spectral band intensities, and thus quantitatively determined. The silver-doped SER-active sol-gels employed in the filled glass capillaries of the apparatus described are prepared in accordance with the method described in the above-identified Farquharson et al. patent. In essence, a silver amine complex, consisting of a 5:1 v/v solution of 1 N $AgNO_3$ and 28% $NH_3OH$, was mixed with an alkoxide, consisting of a 2:1 v/v solution of methanol and tetramethyl orthosilicate (TMOS) in a 1:8 v/v silver amine:alkoxide ratio. As an example of a fabrication technique that can be used in the practice of the invention, a 0.15 mL aliquot of the foregoing mixture is drawn into a 1-mm diameter glass capillary, to fill a 15-mm length, and the silver ions are reduced after sol-gel formation.

Figure 1:
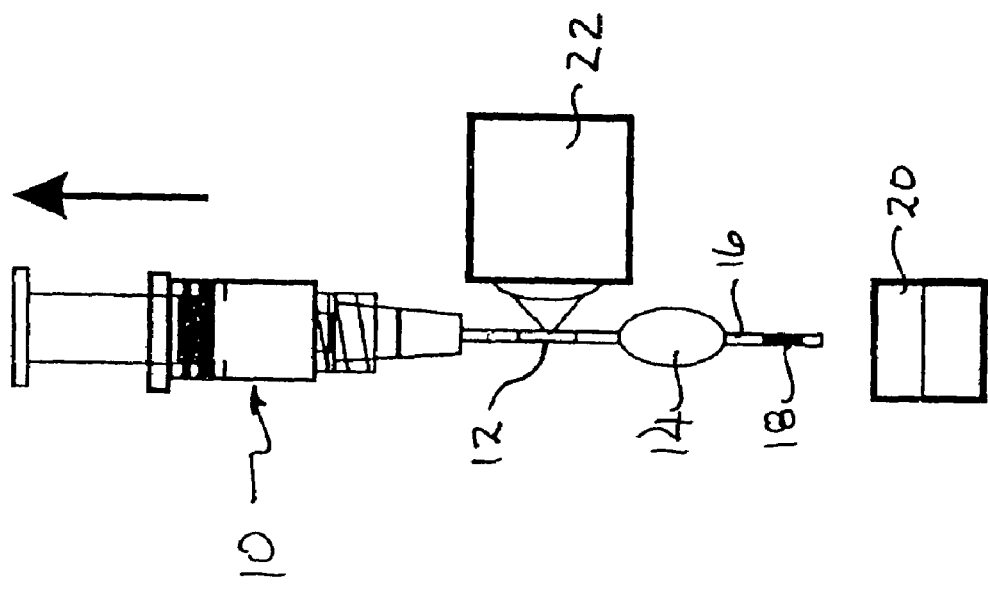
FIG. 1 of the drawings diagrammatically illustrates apparatus and procedures embodying the invention, wherein the apparatus comprises a capillary segment having a pre-weighed reference chemical deposited in its sample-entrance portion, a mixing chamber, a second capillary segment filled or internally coated with a SER-active material, a syringe to effect transport of the analyte solution, and a Raman instrument.

Turning now in detail to FIG. 1 of the appended drawings, therein illustrated is apparatus embodying the invention and comprised of a syringe, generally designated by the number 10, fitted to one end of a SER-active material filled glass capillary segment 12, a mixing chamber 14 and a capillary segment 16, containing a predefined mass 18 of a soluble reference chemical, being attached in series to the opposite end of the capillary segment. In use, the syringe 10 serves to draw, from a surface or vessel 20, a predefined volume of a solution containing an unknown concentration of an analyte chemical, the solution passing through the capillary segment 16 so as to dissolve the mass 18 of the reference chemical, and then to carry the analyte solution and the reference chemical into the mixing chamber 14 and thereafter into the sol-gel filled capillary segment 12. The apparatus is then placed in an appropriate sample holder (not shown) of the Raman instrument (spectrometer) 22, and the surface-enhanced Raman spectrum of the homogeneous sample is generated and recorded, at and from a common field of view within the capillary segment 12, by otherwise conventional means.

Figure 2:
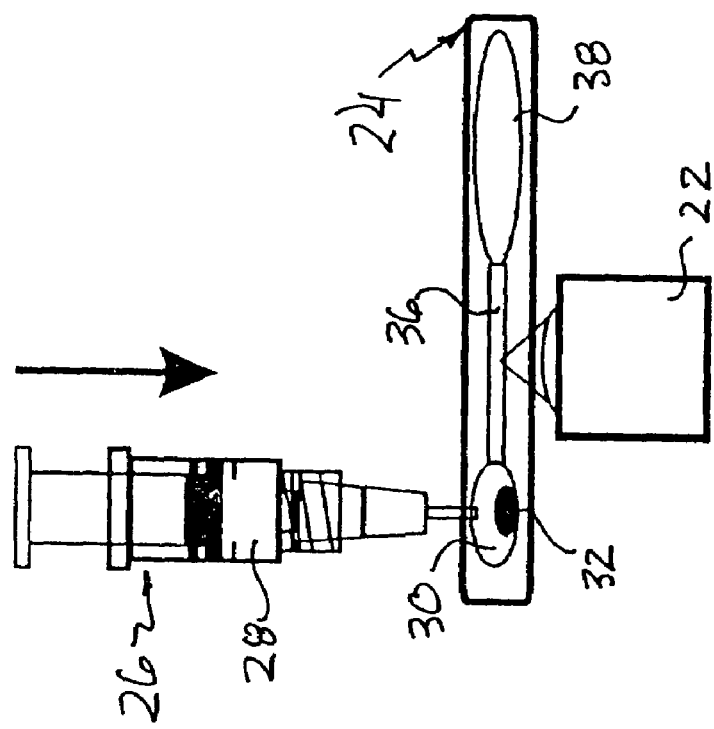
FIG. 2 illustrates diagrammatically another form of apparatus and procedure embodying the invention, wherein the apparatus comprises a reference solution reservoir within a microchip, a SER-active channel within the chip, a syringe to effect solution transport, and a Raman instrument.

A second SER-active device embodying the invention and adapted for use to obtain quantitative measurements of a solution is depicted diagrammatically in FIG. 2 and takes the form of a microchip, generally designated by the numeral 24. A syringe, generally designated by the number 26, contains in its barrel 28 a predefined volume of a solution of an unknown concentration of an analyte chemical and is used to inject the analyte solution into a mixing chamber 30 built into the microchip 24 and containing a predefined mass 32 of a soluble reference chemical. The test solution that results from dissolution of the reference chemical mass 32 in the analyte solution flows through a micro-channel 36 filled with a SER-active material and into an overflow chamber 38 (provided to afford pressure relief during the solution-transport steps), both the micro-channel 36 and also the chamber 38 being built into the micro-chip 24. The microchip 24 is then placed in an appropriate sample holder of a Raman instrument 22 with the micro-channel 36 in its field of focus, enabling the surface-enhanced Raman spectrum of the homogeneous sample to be obtained and recorded.

It will of course be appreciated that variations and modifications of the particular apparatus and techniques described are wholly within the concepts of the present invention. For example, as a variant of the apparatus of FIG. 1 the syringe 10 may first be used to draw a sample into its barrel and then, after connection to the capillary section 16 near the reference chemical mass 18, to force the analyte solution through the reference chemical mass 18, into the mixing chamber 14, and finally into the sol-gel coated capillary 12, the apparatus thus functioning in much the same manner as the microchip apparatus of FIG. 2.

Figure 3:
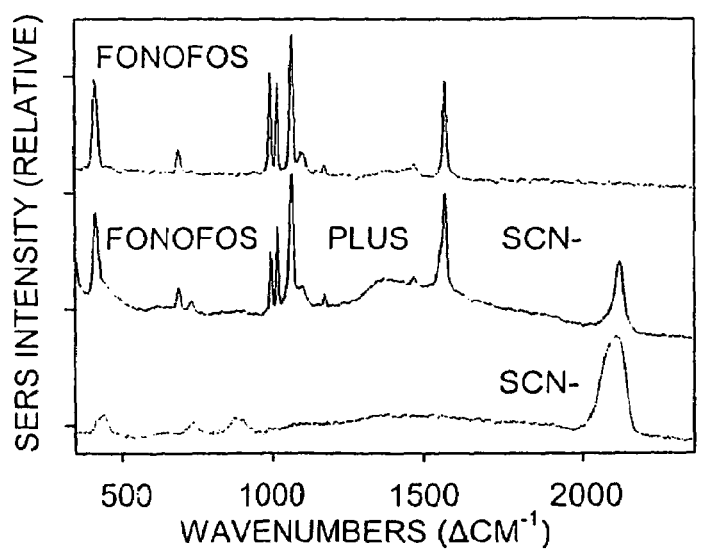
FIG. 3 is a plot of curves showing the surface-enhanced Raman spectra of FONOFOS (o-ethyl-S-phenyl-ethylphosphonodithioate) alone, FONOFOS with SCN⁻ added, and SCN⁻ alone, which illustrates the non-spectral interference of the SCN⁻ added to FONOFOS as the analyte.

Illustrative of analyses that can be carried out using the present apparatus is the following: A reference chemical solution consisting of 0.1 mg of KSCN per mL of water (equivalent to 100 ppm), and an analyte chemical solution consisting of 1.0 microL of FONOFOS per mL of methanol (also equivalent to 100 ppm), are prepared. The reference solution is enclosed in a capillary segment of the apparatus, which is punctured just prior to use to permit the analyte solution to be drawn thereinto and mixed with the reference solution therein. The mixture flows into a segment containing a SER-active material, and the SER spectrum of the mixed solution is measured, using 100 mW of 785 nm laser excitation, and recorded. The resultant curve is presented in FIG. 3, together with curves of the SER spectra of the pure solutions (included to illustrate that the spectral bands of the two chemicals do not overlap), measured under the same conditions. It is found that the SER intensity of the 2095 cm$^{-1}$ band of SCN is 45% of the SER intensity of the 996 cm$^{-1}$ band of FONOFOS, indicating that the term ($I^{SER}_{RS}/I^{SER}_{AS}$) from Equation I equals 0.45.

Figure 4:
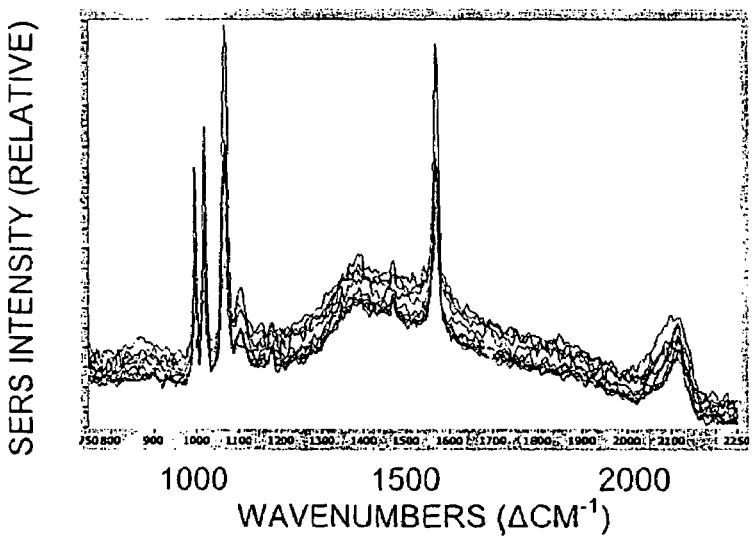
FIG. 4 is a plot of curves showing the surface-enhanced Raman spectra of 100 ppm (0.01% v/v) FONOFOS in methanol plus 100 ppm (0.1 mg/mL) KSCN in water, measured at ten positions (albeit not discriminated in the Figure) along a silver-doped sol-gel filled capillary.

FIG. 4 shows the SER spectra for a solution of 10 ppm SCN and an unknown amount of FONOFOS, produced by dissolving a known amount of a solid reference chemical in a known volume of the analyte chemical solution, measurements being made at ten different points along the length of a SER-active capillary. The spectra are all displayed on the same intensity scale, and (although not readily discernable individually) the measured SER intensity of the 996 cm$^{-1}$ band of FONOFOS varies from 0.12 to 0.4, with an average value of 0.25 and a standard deviation of 20%. At a first position it is found that the SER intensity of the primary FONOFOS band (peak) at 996 cm$^{-1}$ is 125% as intense (as represented by band height) as is the SCN band at 2095 cm$^{-1}$, indicating that the term ($I^{SER}_{AMes}/I^{SER}_{RMeas}$) in Equation I equals 1.25; application of Equation I to calculate the FONOFOS concentration gives a value of 1.25×0.45×10 ppm, or 5.6 ppm. Indeed, the sample employed was prepared as a 5.5 ppm solution, and after referencing each spectrum to SCN an average value of 5.6 ppm is obtained with a standard deviation of 0.15 ppm, or 4%.

Figure 5:
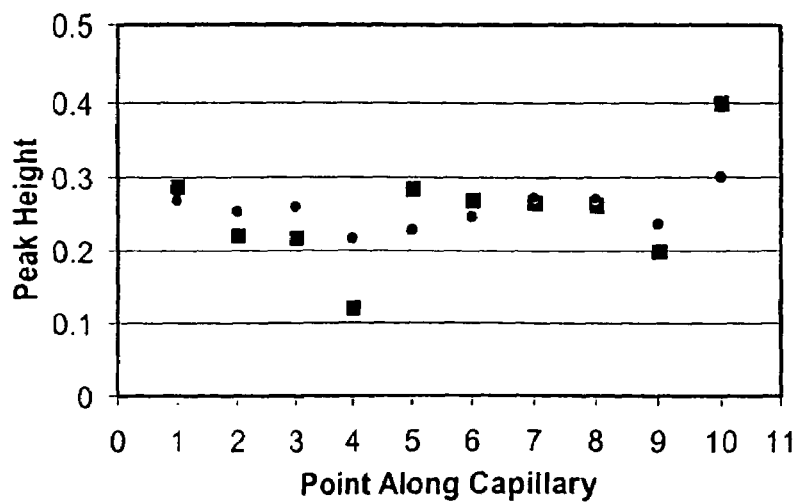
FIG. 5 is a plot illustrative of the intensity of the FONOFOS 996 $cm^{-1}$ peak height at each selected position, both "as-is" and also as referenced to the SCN peak height at 2095 $cm^{-1}$, by division.

FIG. 5 indicates that the incorporation of a trace amount of a reference chemical of known or measurable surface enhancement (e.g., 1 ppm of KSCN) into a solution of an analyte (e.g., FONOFOS) can greatly increase the reproducibility of the concentration measurement. This may be demonstrated by the substantially reduced variability in the intensity measurements obtained from the reference chemical-containing solution (indicated by the circular symbols) at the several irradiation and collection points along the capillary, as compared to the "as is" solution (indicated by the square symbols).

In general, in the practice of the present method, a solution containing at least one analyte chemical and a reference chemical, each chemical exhibiting a substantial and effective surface-enhanced Raman factor, is added to a surface-enhanced Raman-active medium, which is irradiated with excitation radiation to generate SER scattered radiation. At least a portion of the scattered radiation is collected from a common field of view, and analyzed to determine the presence (and usually the concentration) of the analyte chemical in the solution.

The SER-active medium may consist of metal particles or morphologies on a substrate, suspended in a solution (such as a colloid), or incorporated into a porous stationary medium (such as a polymer or sol-gel). In most instances, a sol-gel will preferably be synthesized utilizing a silica-, titania-, or zirconia-based alkoxide, and in certain cases the alkoxide will advantageously employ chemical functional groups that yield chemical selectivity by the synthesized sol-gel.

The SER-active metal, utilized for affording surface-enhanced Raman scattering activity to the Raman-active medium, will normally be silver, gold, copper, nickel, or an alloy or mixture thereof. The metal will usually be of particulate form, preferably of submicron size, with the particles being either substantially isolated from one another or grouped for possible improvement of SER scattering. Such groupings can range in character from random to ordered, such as aggregates or patterned arrangements (e.g., linear or branched).

The SER-active sample apparatus will generally consist of the SER-media coated on the inside walls of a capillary or micro-channel, or contained in a capillary or micro-channel, and will allow for introducing a sample solution thereinto. The apparatus will also have at least at one location optical access that is sufficiently transparent to excitation radiation to permit transmission thereof for generating measurable amounts of surface-enhanced Raman scattered radiation, and it will be sufficiently transparent to such SER radiation, preferably at the same location, to permit transmission of measurable amounts of such scattered radiation. One or more suitable optical devices, capable of delivering excitation radiation and of collecting Raman photons, will be used and may comprise a lens, a microscope objective, a fiber optic probe, etc.

Thus, it can be seen that the present invention provides a novel apparatus and method for effecting SERS, whereby precisely reproducible SER spectral measurements can readily be derived. The apparatus and method of the invention obviate the need for exact replication and stable maintenance of the SER-active materials, so as to enable consistent and substantially invariant SER-scattering analyses to be made, and they enable the detection and quantification of analytes in very low quantities or concentrations, in a manner that is highly effective, precise, reliable, facile and convenient.

Having thus described the invention, what is claimed is:

1. Apparatus for use in effecting surface-enhanced Raman spectroscopy, comprising first and second containment means, said first containment means having a liquid-flow entrance thereinto and an exit therefrom, and containing a known quantity of a reference chemical having an effective surface-enhanced Raman factor; said second containment means containing a surface-enhanced Raman-active medium and having a liquid-flow entrance thereinto, operatively connected to said exit from said first containment means, and an exit therefrom, said second containment means being sufficiently transparent, at least at one optical access location, to permit both the excitation irradiation of, and also the collection of surface-enhanced Raman scattered radiation from, a common field of view of said surface-enhanced Raman-active medium contained therewithin; said apparatus comprising a structure being constructed for effecting intimate mixing, substantially prior to introduction to said surface-enhanced Raman-active medium contained in said second containment means, of said reference chemical with an analyte chemical-containing solution introduced through said entrance into said first containment means.

2. The apparatus of claim 1 wherein said structure for effecting intimate mixing includes a separate mixing chamber operatively interposed between said first and second containment means.

3. The apparatus of claim 1 wherein said first and second containment means are tubular sections.

4. The apparatus of claim 3 wherein said tubular sections are capillaries.

5. The apparatus of claim 1 wherein said structure for effecting intimate mixing includes a mixing chamber and is at least a part of said first containment means.

6. The apparatus of claim 5 additionally including third containment means having an entrance thereinto operatively connected to said exit from said second containment means, said third containment means serving as an overflow chamber.

7. The apparatus of claim 1 wherein said reference chemical is in the form of a solid mass that is completely and readily soluble in the analyte chemical-containing solution to form a homogeneous test solution.

8. The apparatus of claim 1 wherein said reference chemical is in the form of a solution with which the analyte chemical-containing solution is completely miscible to form a homogeneous test solution.

9. The apparatus of claim 1 additionally including liquid transport means operatively connected to at least one of said entrance into said first containment means, for injecting the analyte chemical-containment solution thereinto, and said exit from said second containment means for effecting evacuation thereof.

10. The apparatus of claim 9 wherein said liquid transport means comprises a syringe.

11. The apparatus of claim 1, wherein said apparatus is incorporated into a microchip.

12. The apparatus of claim 1 wherein said reference chemical comprises a thiocyanate or cyanide compound that is soluble in said analyte solution.

13. The apparatus of claim 12 wherein said compound is a salt or an inorganic complex.

14. The apparatus of claim 13 wherein said compound is selected from the group consisting of thiocyanate salts of sodium, potassium and calcium; cyanide salts of sodium, potassium and calcium; sodium ferrocyanide; potassium hexacyanoruthenate; and pentacyanoferrothiocyanate.

15. The apparatus of claim 1 wherein said surface enhanced Raman-active medium comprises a metal selected from the group consisting of copper, gold, silver, nickel, and alloys and mixtures thereof.

16. The apparatus of claim 15 wherein said metal is of particulate form, or is in the form of a surface having a morphology functionally equivalent to metal particles.

17. The apparatus of claim 1 wherein said surface-enhanced Raman-active medium comprises a sol-gel synthesized utilizing a silica-based, titania-based, or zirconia-based alkoxide, and at least one surface-enhanced Raman-active metal.

18. In a method for effecting surface-enhanced Raman spectroscopy, the steps comprising:
providing apparatus comprised of first and second containment means, said first containment means having a liquid-flow entrance thereinto and an exit therefrom and containing a known quantity of a reference chemical having an effective surface-enhanced Raman factor; said second containment means containing a surface-enhanced Raman-active medium and having a liquid-flow entrance thereinto, operatively connected to said exit from said first containment means, and an exit therefrom, said second containment means being sufficiently transparent, at least at one optical access location, to permit both the excitation irradiation of, and also the collection of surface-enhanced Raman scattered radiation from, a common field of view of said surface-enhanced Raman-active medium contained therewithin; said apparatus being constructed for effecting intimate mixing, substantially prior to introduction to said surface-enhanced Raman-active medium contained in said second containment means, of said reference chemical with an analyte chemical-containing solution introduced through said entrance into said first containment means;
providing a solution of an analyte chemical of an unknown concentration;
applying positive or negative pressure to said apparatus comprising a structure in such a manner as to cause a known volume of said analyte chemical-containing solution to be introduced into said first containment means, as to cause said reference chemical contained in said first containment means to disperse homogeneously with said analyte chemical-containing solution and to form a homogeneous test solution, and as to cause said homogeneous test solution to be transported into said second containment means and to permeate said surface-enhanced Raman-active medium contained therein;
irradiating said surface-enhanced Raman-active medium, permeated by said homogeneous test solution, at said common field of view with excitation radiation so as to produce surface-enhanced Raman scattered radiation; and
collecting a measurable amount of said surface-enhanced Raman scattered radiation produced from said common field of view.

19. The method of claim 18 wherein said reference chemical contained in said first containment means is in the form of a solid mass that is completely and readily soluble in said analyte chemical-containing solution, and wherein said step of dispersing is effected by flowing said analyte chemical-containing solution in intimate contact with said reference chemical mass.

20. The method of claim 18 wherein said reference chemical is in the form of a solution with which said analyte solution is completely miscible, and wherein said step of dispersing is effected by introducing said analyte chemical-containing solution into said reference chemical solution.

21. The method of claim 18 wherein said reference chemical comprises a thiocyanate or cyanide compound that is soluble in said analyte solution.

22. The method of claim 21 wherein said compound is a salt or an inorganic complex.

23. The method of claim 22 wherein said compound is selected from the group consisting of thiocyanate salts of sodium, potassium and calcium; cyanide salts of sodium, potassium and calcium; sodium ferrocyanide; potassium hexacyanoruthenate; and pentacyanoferrothiocyanate.

24. The method of claim 18 wherein said surface enhanced Raman-active medium comprises a metal selected from the group consisting of copper, gold, silver, nickel, and alloys and mixtures thereof.

25. The method of claim 24 wherein said metal is of particulate form, or is in the form of a surface having a morphology functionally equivalent to metal particles.

26. The method of claim 18 wherein said surface-enhanced Raman-active medium comprises a sol-gel synthesized utilizing a silica-based, titania-based, or zirconia-based alkoxide, and at least one surface-enhanced Raman-active metal.

* * * * *

UNITED STATES PATENT AND TRADEMARK OFFICE
CERTIFICATE OF CORRECTION

PATENT NO.         : 7,312,088 B2
APPLICATION NO. : 10/902511
DATED              : December 25, 2007
INVENTOR(S)       : Stuart Farquharson Page 1 of 1

It is certified that error appears in the above-identified patent and that said Letters Patent is hereby corrected as shown below:

In Claim 1, at line 46 of column 12, and also in Claim 18, at line 58 of column 13, the words "being constructed" should be deleted. The phrase "comprising a structure" should appear in Claim 18, at line 58 of column 13, and that phrase should be deleted from Claim 18, at line 7 of column 14.

Signed and Sealed this

Twenty-ninth Day of April, 2008

JON W. DUDAS
*Director of the United States Patent and Trademark Office*